US012667346B2

(12) United States Patent
Ruers et al.

(10) Patent No.: US 12,667,346 B2
(45) Date of Patent: Jun. 30, 2026

(54) SURGICAL INSTRUMENT AND SURGICAL SYSTEM

(71) Applicant: Stichting Het Nederlands Kanker Instituut—Antoni van Leeuwenhoek Ziekenhuis, Amsterdam (NL)

(72) Inventors: Theodoor Jacques Marie Ruers, Amsterdam (NL); Henricus Josephus Cornelus Maria Sterenborg, Amsterdam (NL); Wouter Johannes Heerink, Amsterdam (NL)

(73) Assignee: Stichting Het Nederlands Kanker Instituut—Antoni van Leeuwenhoek Ziekenhuis, Amsterdam (NL)

(*) Notice: Subject to any disclaimer, the term of this patent is extended or adjusted under 35 U.S.C. 154(b) by 1014 days.

(21) Appl. No.: 16/963,519

(22) PCT Filed: Jan. 24, 2019

(86) PCT No.: PCT/NL2019/050041
§ 371 (c)(1),
(2) Date: Jul. 21, 2020

(87) PCT Pub. No.: WO2019/147129
PCT Pub. Date: Aug. 1, 2019

(65) Prior Publication Data
US 2021/0045721 A1 Feb. 18, 2021

(30) Foreign Application Priority Data
Jan. 26, 2018 (NL) ..................................... 2020329

(51) Int. Cl.
A61B 10/02 (2006.01)
A61B 10/00 (2006.01)
(Continued)

(52) U.S. Cl.
CPC ...... *A61B 10/0283* (2013.01); *A61B 10/0275* (2013.01); *A61B 34/30* (2016.02);
(Continued)

(58) Field of Classification Search
None
See application file for complete search history.

(56) References Cited

U.S. PATENT DOCUMENTS 5,983,125 A 11/1999 Alfano et al.
6,840,948 B2 * 1/2005 Albrecht ................ A61B 18/14
600/568
(Continued)

FOREIGN PATENT DOCUMENTS

CN 106198360 A 12/2016
WO WO-2013108194 A2 * 7/2013 ......... A61B 18/1402
(Continued)

*Primary Examiner* — Jason M Sims
*Assistant Examiner* — Matthew Eric Ogles
(74) *Attorney, Agent, or Firm* — Ipsilon USA—NLO

(57) ABSTRACT

A surgical instrument is disclosed to remove tissue, in particular unhealthy tissue or tissue containing cancer cells, from a body and to analyse the removed tissue. A tissue removal device is arranged at a distal end of the surgical instrument, wherein the distal part of the surgical instrument comprises a movable part, for example a bendable part, to adjust a position and/or orientation of the tissue removal device with respect to a proximal end of the surgical instrument, wherein movement of the movable part can be controlled by an operator. A discharge channel is connected to the tissue removal device for discharge of removed tissue. A tissue analysis device comprises an analysis sensor to analyse non-removed tissue in front of the tissue removal device, wherein the tissue analysis device is configured to provide a sensor signal representative for an analysed characteristic of the tissue.

17 Claims, 10 Drawing Sheets

(51) Int. Cl.

| | | |
|---|---|---|
| *A61B 17/32* | (2006.01) | |
| *A61B 34/20* | (2016.01) | |
| *A61B 34/30* | (2016.01) | |

(52) U.S. Cl.

CPC ..................... *A61B 10/0041* (2013.01); *A61B 2017/320064* (2013.01); *A61B 2034/2072* (2016.02)

(56) References Cited

U.S. PATENT DOCUMENTS

| | | | | |
|---|---|---|---|---|
| 9,730,756 B2 * | 8/2017 | Ben Oren | .............. | A61B 18/24 |
| 2006/0013523 A1 * | 1/2006 | Childlers | .......... | G02B 6/02042 |
| | | | | 385/12 |
| 2007/0156019 A1 | 7/2007 | Larkin et al. | | |
| 2007/0287933 A1 * | 12/2007 | Phan | .............. | A61B 17/320016 |
| | | | | 600/564 |

| | | | | |
|---|---|---|---|---|
| 2008/0249553 A1 * | 10/2008 | Gruber | .................. | A61M 1/842 |
| | | | | 606/171 |
| 2010/0081964 A1 * | 4/2010 | Mark | ................. | A61B 10/0283 |
| | | | | 600/566 |
| 2010/0317964 A1 * | 12/2010 | Hendriks | ............. | A61B 5/6848 |
| | | | | 600/567 |
| 2014/0024951 A1 * | 1/2014 | Herzlinger | ......... | A61B 1/00096 |
| | | | | 600/478 |
| 2015/0005765 A1 * | 1/2015 | Hendriks | ........... | A61B 18/1402 |
| | | | | 606/41 |
| 2015/0359525 A1 * | 12/2015 | Hendriks | ............. | A61B 5/6848 |
| | | | | 600/478 |
| 2017/0035399 A1 * | 2/2017 | Mak | ..................... | A61B 5/4887 |
| 2017/0319186 A1 | 11/2017 | Van Der Zaag et al. | | |
| 2019/0041319 A1 * | 2/2019 | Ruers | .................... | G01N 21/49 |

FOREIGN PATENT DOCUMENTS

| | | | | |
|---|---|---|---|---|
| WO | 2014/068468 A1 | 5/2014 | | |
| WO | WO-2017142399 A1 * | 8/2017 | ......... | G01N 21/4795 |

* cited by examiner

Figure 2

SURGICAL INSTRUMENT AND SURGICAL SYSTEM

The present invention relates to a surgical instrument and a surgical system to remove tissue, in particular tissue containing cancer cells from a body of a patient and to analyse the removed tissue.

One in three Europeans will develop cancer, the majority of which will be treated with surgery. Despite impressive progress in diagnostic imaging, tumour tissue can often not be identified during surgery. In up to 30% of cases tumour tissue is left behind erroneously, causing a large amount of secondary procedures. For breast cancer alone 100,000-200,000 reoperations take place annually in the US and Europe.

For breast cancer treatment there is a strong tendency to more minimalised treatment. The surgical treatment is moving from complete breast amputation in the past to breast conserving surgery by removing the tumor as a small breast lump. But even with removal of only the breast tumor lump, the cosmetic outcome may be disappointing.

An important challenge during cancer surgery is to find an accurate surgical resection plane. To this end pre-operative imaging information has to be translated to the real time view during surgery. Currently, this is performed within the surgeon's mind with clearly limited capacities in 3-D visualization and tissue recognition.

WO2013/108194 A2 discloses an electro-surgical system with an optical feedback functionality for performing electro-surgery on tissue of a patient. The electro-surgical device of this system has an electrode portion with an optical guide integrated therein. An optical unit performs optical characterization of tissue type and/or condition, and is arranged for performing an in vivo analysis of the tissue type and/or condition. Therefore, the optical guide allows inspecting the tissue that is e.g. just a few millimeters ahead of the electrode portion before actual removal of the tissue e.g. by cutting The electro-surgical system of WO2013/108194 A2 provides analysis performed by a spectrometer provided in the optical unit. The system can proactively react to what kind of tissue is in front of the electro-surgical device.

A drawback of the electro-surgical system of WO2013/108194 A2 is that, in practice, it is difficult to exactly remove the tissue part that is analysed in front of the electro-surgical portion. It is possible that non-healthy tissue still remains in the body of the patient or that a substantial part of the removed tissue is healthy tissue.

Another drawback of the electro-surgical device of WO2013/108194 A2 is that at least a substantial part of the tissue that is analysed will be destructed during removal of the tissue, due to the electric current that is applied by the electro-surgical portion of the electro-surgical device to the tissue in order to cut, coagulate, desiccate, and/or fulgurate the tissue. The destructed tissue cannot be used for molecular analysis post-surgery, which is, for example, increasingly important in modern breast cancer care.

An aim of the present invention is to provide a surgical instrument that may improve the outcome of cancer surgery. In particular, it is an aim of the invention to provide a surgical instrument that lack one or more of the above-mentioned drawbacks of the electro-surgical device of WO2013/108194 A2, or at least to provide an alternative.

An aspect of the present invention provides a surgical instrument to remove tissue, in particular unhealthy tissue or tissue containing cancer cells, from a body and to analyse the removed tissue, comprising:

a tissue removal device arranged at a distal end of the surgical instrument, wherein the distal part of the surgical instrument comprises a movable part, for example a bendable part, to adjust a position and/or orientation of the tissue removal device with respect to a proximal end of the surgical instrument, wherein movement of the movable part can be controlled by an operator;

a discharge channel connected to the tissue removal device for discharge of removed tissue; and a tissue analysis device comprising an analysis sensor to analyse non-removed tissue in front of the tissue removal device, wherein the tissue analysis device is configured to provide a sensor signal representative for an analysed characteristic of the tissue, in particular for the presence of unhealthy tissue or cancer cells within the tissue.

Another aspect of the present invention provides a first surgical instrument for cooperating with a second surgical instrument, the first instrument comprising a needle having a form of a hollow shaft comprising an outer wall around an inner cavity, an interior of the needle providing a space for positioning the second surgical instrument coaxially to the needle at least partly inside the needle and movable with respect to the needle in an axial direction of the needle; and a tissue analysis device comprising an analysis sensor to analyse non-removed tissue at a distal tip of the needle, wherein the tissue analysis device is configured to provide a sensor signal representative of an analysed characteristic of the tissue, in particular for the presence of unhealthy tissue or cancer cells within the tissue.

An aspect of the present invention provides a surgical instrument to remove tissue, in particular tissue containing cancer cells, from a body and to analyse the removed tissue, comprising:

a tissue removal device arranged at a distal end of the surgical instrument;

a discharge channel connected to the tissue removal device for discharge of removed tissue; and a tissue analysis device, comprising an analysis sensor arranged to analyse removed tissue passing through the discharge channel, wherein the tissue analysis device is configured to provide a sensor signal representative for an analysed characteristic of the removed tissue, in particular for the presence of cancer cells within the removed tissue.

The surgical instrument of the invention is configured to remove tissue, in particular tissue containing cancer cells, from a body of the patient. Furthermore, certain embodiments of the surgical instrument are capable of ex-vivo nearly real-time analysis of the removed tissue, i.e. relatively shortly after removing the tissue from the body of the patient. This analysis of the removed tissue may therefore directly provide feedback on the analysed characteristic of the removed tissue. This feedback enables the operator to determine whether he should continue or stop removing tissue in a certain direction.

The surgical instrument may also be part of a robotic surgical system. In such robotic surgical system, the feedback may correspondingly be used to determine whether removal of tissue in a certain direction should be continued or should be stopped.

An advantage of the tissue analysis device of the surgical instrument of the invention is that the analysis takes place after the tissue has been taken out of the body of the patient.

This ensures that the analysed tissue is also exactly the tissue that is removed from the body of the patient.

A further advantage of the surgical instrument is that the pieces of tissue that are removed from the body of the patient will remain intact during analysis when passing by the analysis sensor. As a result, the tissue can still be used for additional analysis post-surgery, such as molecular analysis, which is, for example, increasingly important in modern breast cancer care.

Another advantage of the surgical instrument of the invention is that the tissue analysis device with ex-vivo analysis may be more suitable to detect forms of cancer that are generally more difficult to detect. For example, small pockets of a typical form of cancer, so called Ductal Carcinoma in situ (DCIS) are difficult to detect in vivo with known in vivo techniques. The tissue analysis device of the surgical instrument of the invention provides the possibility to carry out an ex-vivo analysis of removed tissue in a near real-time fashion. The results of this ex-vivo analysis can directly be used to provide feedback to the surgeon or a surgical robot system that operates the surgical instrument.

To remove tissue from the body of the patient a tissue removal device is provided at the distal end of the surgical instrument. The tissue removed by this tissue removal device is fed into a discharge channel connected to the tissue removal device for discharge of the removed tissue. The discharge channel may for example be formed by one or more tubes or conduits.

The surgical instrument further comprises a tissue analysis device comprising an analysis sensor to analyse removed tissue passing through the discharge channel. The analysis sensor is capable of analysing the removed tissue ex-vivo shortly after the tissue has been removed from the body of the patient. The tissue analysis device is configured to provide a sensor signal representative for a characteristic of the removed tissue.

The sensor signal for example enables the operator to monitor whether removed tissue passing through the discharge channel contains cancer cells. As soon as the sensor signal indicates that no more cancer cells are present in the removed pieces of tissue passing along the analysis sensor, the tissue removal device can be controlled to prevent that more healthy tissue is unnecessarily removed from the body of the patient. Controlling the tissue removal device may comprise stopping the removal action of the tissue removal device, but may also involve adapting an orientation and/or direction of movement of the tissue removal device with respect to the tissue of the body of the patient.

The above approach using nearly real-time ex-vivo analysis of the removed tissue may produce clean resection margins with a minimal removal of healthy tissue and hence optimal cosmetic result.

The results of the tissue analysis may for example be available within 60 seconds, preferably within 30 seconds, or even more preferably within 15 seconds after removal of the tissue. This allows the operator to adapt the position of the surgical instrument to the outcome of the analysis. In practice, the operator may remove tissue at a location, wait for the outcome of the tissue analysis and dependent on the outcome of the tissue analysis determine a new location for tissue removal. The operator may be a human or robotic operator.

In alternative embodiments, the surgical instrument may be arranged to monitor whether removed tissue comprises another characteristic and, when desired stop removal of tissue when the removed tissue no longer comprises the analysed characteristic.

The analysis sensor may comprise any technique that is suitable to determine in line, i.e. while a piece of tissue is passing through a discharge channel, whether or not the removed tissue passing the analysis sensor comprises a certain analysed characteristic. Known technologies may provide near real-time results, enabling the operator to stop the removal of tissue that should not be removed.

In an embodiment the analysis sensor is a fiber optic spectroscopy sensor or a hyperspectral imaging sensor, or fibres and a sensor in particular for use in Diffuse Reflectance Spectroscopy (DRS).

It has been found that hyperspectral imaging, in a wavelength range between 940 nm and 1650 nm, is suitable for use in optical measurements to detect carcinoma, e.g. cancer cells, in tissue specimen. This ex-vivo hyperspectral imaging may also be combined with a known method for optical imaging, as is described in US 2019/0041319, the contents of which are herein incorporated by reference, in its entirety.

In recent research by the applicant, tissue specimen of 18 breast cancer patients were cut in 5 mm thick slices in order to allow for hyperspectral imaging of the cut surfaces and to perform a pixel-by-pixel correlation with conventional histopathological measurements. A support vector machine (SVM) classification algorithm was developed on the basis of the correlation, with which an overall diagnostic accuracy of 91% was achieved between the hyperspectral imaging and the histopathological measurements.

The hyperspectral imaging was then used to image unsliced tissue specimen from 6 additional patients and the obtained SVM classification algorithm was used to classify the specimen. The algorithm classified, based on the hyperspectral imaging, the specimen as tumour positive correctly in all of them, except for one. In the latter specimen, it was later detected with histopathological measurements, that a cancer pocket with a size of 1 mm was present therein.

It has been found that Diffuse Reflectance Spectroscopy in the near infrared wavelength region is suitable as well for use in optical measurements in a surgical environment. This technique is described in more detail in "Diffuse reflectance spectroscopy: towards clinical application in breast cancer.", Evers D. J., et al., Breast Cancer Res Treat. 2013 January; 137(1):155-65, "Fat/Water ratios measured with diffuse reflectance spectroscopy to detect breast tumor boundaries.", de Boer L. L. et al., Breast Cancer Res Treat. 2015 August; 152(3):509-18, and "Using DRS during breast conserving surgery: identifying robust optical parameters and influence of inter-patient variation," de Boer L. L. et al., Biomedical Optics Express 7, 5188-5200 (2016), all contents of which are herein incorporated by reference. In the latter, for example, it has been found that this in vivo detection of breast cancer may be performed with DRS in a broad spectral range, having wavelengths between 450 nm and 1700 nm.

In another embodiment, the analysis sensor is a Raman Spectroscopy sensor or a MicroCT imaging device.

In particular, when it is desired to detect forms of cancer that are generally more difficult to detect, a Raman Spectroscopy sensor or a MicroCT imaging device may also be applied. MicroCT imaging may for example be used ex vivo to detect Ductal Carcinoma in situ in the removed tissue based on the microcalcifications that characterize Ductal Carcinoma in situ.

In an embodiment, the surgical instrument comprises an elongate housing, wherein the discharge channel at least partially runs through the housing, and wherein the tissue analysis device is arranged in the housing. To prevent that unhealthy tissue is unnecessarily removed from the body of the patient, it is desirable that a length of the discharge channel between the tissue removal device and the location of the analysis sensor is short so that the travelling time of the removed tissue from the tissue removal device to the analysis sensor is also short. By placing the tissue analysis device in the housing, the tissue analysis device can be arranged at a relatively short distance from the tissue removal device. This allows to analyse the tissue quickly after removal of the tissue from the body of the patient.

In an alternative embodiment, the tissue analysis device is arranged outside the housing. For example, when the tissue analysis device is relatively large or heavy it may be advantageous to place the tissue analysis device outside the housing, for example at a stationary position. The time needed between removal of tissue and analysis of the tissue may in such case be longer due to the time needed to transport the removed tissue to the tissue analysis device. However, it has been found that this time may be sufficiently small to use the outcome of the tissue analysis device as input for manoeuvring the surgical instrument for the removal of tissue.

In an embodiment, the tissue removal device comprises a suction device. The suction device may be any device that creates a suction flow at or near the distal end of the discharge channel to ensure that the pieces of tissue that are removed from the body of the patient are drawn into the discharge channel such that the pieces of tissue do not remain in the body of the patient, but are discharged while passing along the analysis sensor enabling the analysis sensor to analyse the removed tissue.

The suction device may also provide sufficient force to remove tissue from the body of the patient without the need for other tools, such as cutting blades, to remove the tissue from the body of the patient.

In an embodiment, the surgical instrument comprises a cutting device. To facilitate removal of tissue from the body of the patient, the tissue removal device may be provided with a cutting device configured to cut pieces of tissue. The cutting device may be any device, for example a rotatable cutting blade, that is capable of cutting pieces of tissue from the body of the patient, at a location where the cut pieces of tissue can easily and reliably move into the distal end of the discharge channel to discharge the pieces of tissue through the discharge channel.

In an embodiment, a proximal end of the discharge channel is connectable to an underpressure source to create a suction flow in the discharge channel. The suction flow in the discharge channel is used to draw pieces of tissue removed from the body of the patient into the discharge channel and to transport the removed tissue from the distal end of the discharge channel along the analysis sensor towards the proximal end of the discharge channel.

The underpressure source may for example be a vacuum pump or a vacuum wall outlet.

In an embodiment, the surgical instrument comprises a second tissue analysis device comprising a second analysis sensor to analyse non-removed tissue in front of the tissue removal device.

The surgical instrument of the present invention comprises a tissue analysis device to analyse whether removed tissue comprises a characteristic of interest, for instance the presence of cancer cells. This analysis takes place with respect to pieces of tissue that are already removed from the body of the patient. It is desirable that additionally the tissue can also be analysed before removal of the tissue.

The surgical instrument may therefor comprise a second analysis device arranged to analyse whether tissue in front of the tissue removal device comprises the characteristic of interest. The analysis of the second analysis device can be used to verify in vivo whether the tissue removal device is in the correct position to remove targeted issue, i.e. tissue to be removed from the body of the patient.

This second tissue analysis device further increases the reliability of the operation of the surgical instrument in removing desired tissue from the body of the patient, without unnecessarily removing healthy tissue.

In an embodiment, the second analysis sensor is a tissue analysis device based on optical techniques, such as a fiber optic spectroscopy device, or a hyperspectral imaging or fluorescent imaging device or multifibre optical devices at the tip of the surgical instrument. Fiber optic spectroscopy, fluorescent imaging, hyperspectral, multispectral or multi-fibre spectroscopy may be used for Diffuse Reflectance Spectroscopy (DRS) or fluorescence imaging or hyperspectral or multispectral imaging in the visible and/or near infrared (NIR) wavelength region. Fluorescence measurements can be based on the native fluorescence of the tissue or may use exogenously administered florescent molecules These analyses will be used to differentiate normal healthy breast tissue form cancerous breast tissue. DRS has proved to be capable of distinguishing in vivo invasive carcinoma from normal tissue based on differences in fat and water content with high accuracy.

The second tissue analysis device may for example be configured as described in US 2015/0005765, the contents of which are herein incorporated by reference, in its entirety.

Any other suitable second analysis sensor arranged to analyse tissue in front of the tissue removal device may also be applied such as pH sensors in all kinds of design or acoustic detectors.

In cancer surgery pre-operative imaging is used to determine the location of a tumor to be removed from the body of the patient. This pre-operative imaging data may be used during surgery to navigate the surgical instrument of the invention to the tissue to be removed.

To automatically track a position of the surgical instrument in order to determine a real-time location of the instrument, the surgical instrument may be provided with one or more tracking markers to enable a position tracking system to track a position of the surgical instrument. These tracking markers may for example be electro-magnetic or optical markers that can be tracked by a position tracking system configured to determine a 3D position of the surgical instrument. The 3D position of the surgical instrument obtained in this way may be combined with the pre-operative image data in order to determine a position of the surgical instrument with respect to the body of the patient, in particular with respect to the tissue to be removed.

In breast surgery, this may be particularly challenging because there are no rigid anatomical references in the vicinity, i.e. bone, and the deformation will increase continuously when instruments are inserted and tissue is removed. As a consequence, the pre-operative image data, may become less reliable to determine the exact position of the tissue to be removed To improve positioning of the surgical instrument with respect to the body of the patient, in particular with respect to breast tissue to be removed, additionally intraoperative ultrasound technology may be used, which enables real time imaging and with the additional possibility of placing ultrasound sensitive fiducials for additional navigation accuracy.

In an embodiment, the surgical instrument comprises a feedback device to provide a signal on the basis of the sensor signal representative for the analysed characteristic of the removed tissue, in particular the presence of cancer cells within the removed tissue. The feedback device may be a light emitting or sound producing element that provides feedback to the operator with respect to the analysed tissue characteristic.

The feedback device may also be a signal output device that is connected to a central processing unit, for example a central processing unit of a surgical robot. The feedback device may provide a feedback signal that enables the surgical robot to manoeuver the surgical instrument on the basis of the analysis of the removed tissue by the tissue analysis device or on the basis of the in vivo tissue analysis by the sensor at the tip of the surgical instrument.

In an embodiment, the distal part of the surgical instrument comprises a movable part, for example a bendable part, to adjust a position and/or orientation of the tissue removal device with respect to a proximal end of the surgical instrument, wherein movement of the movable part can be controlled by an operator.

By providing a movable part at the distal part of the surgical instrument, the position and/or orientation of the tissue removal device may be adapted without the need of repositioning the proximal part of the surgical instrument. This allows a quicker and/or more accurate movement of the tissue removal device from a first removal location to a second removal location.

In an embodiment, the surgical instrument comprises a position sensor system to determine a position of the movable part. It is advantageous for the operator to know the position of the movable part. A position sensor system may be provided to determine this position.

The position sensor system may comprise a relative position sensor that determines a position of the movable part with respect to the proximal end of the surgical instrument. Such relative position sensor may for example comprise one or more fiber Bragg gratings provided in an optical fiber mounted in the movable part. Fiber Bragg gratings provide a phase shift in light reflected by the fiber Bragg gratings in dependence of the stress or strain that is exerted on the part of the optical fiber in which the one or more fiber Bragg gratings are provided. An interrogator device spaced from fiber Bragg gratings but connected to the optical fiber may be used to interrogate the fiber Bragg gratings. On the basis of the measurements of the interrogator device a relative position of the movable part with respect to the proximal part of the surgical instrument may be determined.

In another embodiment, the position sensor system may be configured to determine an absolute position of the movable part, for example by using electromagnetic tracking of the movable part.

In an embodiment, the surgical instrument comprises a tissue treatment device, for example a cryotreatment unit to freeze tissue before removal of the tissue, an electrocoagulation unit and/or an electromagnetic head for emitting radio waves. In some procedures it may be advantageous to treat the tissue before its actual removal, for example to prevent excessive bleeding during or after removal. This treatment may be a cryo-treatment in which the tissue is frozen, or a coagulation treatment in which the tissue is coagulated. Tissue treatment devices, such as a cryo-treatment unit and an electrocoagulation unit are known in the art.

The invention further relates to a surgical system to remove tissue, in particular tissue containing cancer cells, from a body and to analyse the removed tissue, comprising:
    the surgical/interventional instrument of any of the clauses 1-13 or claims 1-14, and an underpressure source connected to a proximal end of the discharge channel to create a suction flow in the discharge channel.

In an embodiment, the surgical instrument comprises one or more tracking markers, and wherein the surgical system comprises a position tracking system to track a position of the surgical instrument using the one or more tracking markers.

In an embodiment, the surgical system comprises a central processing unit configured to monitor and display the in vivo tissue sensing results made at the tip of the surgical instrument. In dependence of the outcome of the in vivo tissue sensing results the central processing unit may indicate to the operator further locations for the removal of tissue. In another embodiment, the surgical system comprises a central processing unit configured to monitor the removal of tissue by the surgical instrument. In dependence of the outcome of the monitoring of the removed tissue, the central processing unit may indicate to the operator further locations for the removal of tissue. In an embodiment, the surgical system is a surgical robot system, wherein the surgical system comprises one or more actuators to control a position of the surgical instrument. In such embodiment, the outcome of the monitoring of the removed tissue, can be used to directly manipulate the surgical instrument to further locations for the removal of tissue.

In an embodiment, the surgical system comprises a receptacle directly or indirectly connected to the discharge channel to collect removed tissue. By collecting all removed tissue in a receptacle, the tissue remains available for further analysis.

An embodiment of a surgical instrument and surgical system according to the invention will now be described in further detail, by way of example only, with reference to the accompanying drawings, in which:

FIG. 2 shows schematically a distal part of an alternative embodiment of a surgical instrument according to the invention;

FIG. 1 shows a surgical instrument according to an embodiment of the invention generally denoted by the reference numeral 1. The surgical instrument 1 is configured to remove tissue from a body of a patient, in particular tissue comprising cancer cells.

Figure 1:
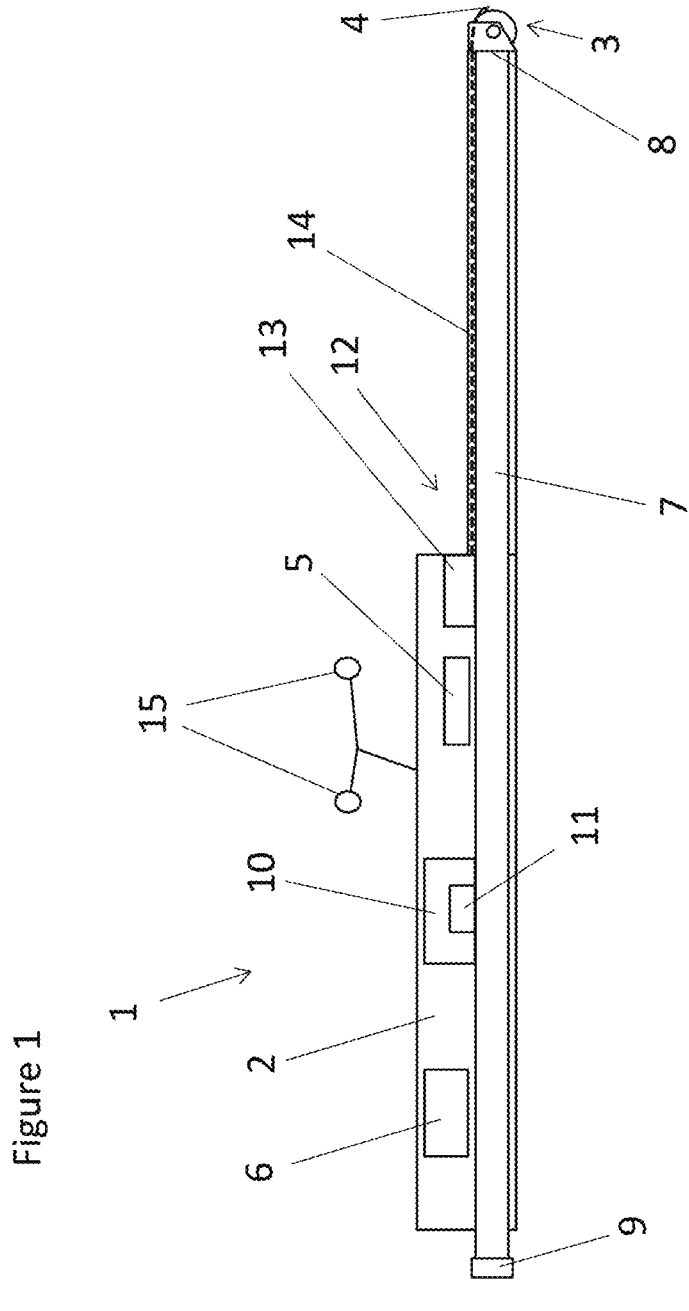
FIG. 1 shows schematically an embodiment of a surgical instrument according to the invention.

The surgical instrument 1 comprises an elongate housing 2 that allows a surgeon to hold the surgical instrument or that may be used to mount the surgical instrument 1 in a surgical robot system. An elongate distal part of the surgical instrument comprises a decreased cross-section and is configured to be brought into a body of the patient.

At the distal end of the surgical instrument 1 a tissue removal device 3 is arranged. The tissue removal device 1 comprises a cutting blade 4 that is mounted on a rotatable element that can be driven in a rotating movement by an actuator 5. The actuator 5 may, for example, be activated by a user of the surgical instrument, for instance by pressing a button, and/or by a processing unit 6 of the surgical instrument 1.

When the tissue removal device 3 is moved in distal direction against tissue and the cutting blade 4 is driven by the actuator 5 in a rotating movement, the cutting blade 4 can cut pieces of tissue from this tissue in front of the tissue removal device 3, i.e. directly distally from the tissue removal device 3.

A discharge channel 7 formed by a tube is connected to the tissue removal device 3 for discharge of removed tissue. The discharge channel 7 runs through the housing 2 from a distal end 8 connected to the tissue removal device 3 to a proximal end 9 configured to be connected to an underpressure source. When an activated underpressure source is connected to the proximal end 9 of the discharge channel 7, a suction flow will come into existence in the discharge channel 7 flowing from the distal end 8 to the proximal end 9 of the discharge channel 7. Due to this suction flow, pieces of tissue cut from the body of the patient will be drawn into the discharge channel 7 and be moved towards the proximal end 9 of the discharge channel 7.

It is remarked that, dependent on the circumstances, the suction flow may also be used to remove tissue from the body of the patient without using any additional tool such as a cutting blade.

When being transported through the discharge channel 7, the removed pieces of tissue will move past a tissue analysis device 10, comprising an analysis sensor 11 arranged to ex vivo analyse removed tissue passing through the discharge channel 7. The analysis sensor 11 provides a sensor signal representative for an analysed characteristic of the removed tissue. The tissue analysis device 10 is in particular configured to determine whether or not cancer cells are present in the piece of removed tissue that passes the analysis sensor 11.

The tissue analysis device 10 of the invention provides feedback of ex vivo tissue analysis relatively shortly after the tissue has been removed from the body of the patient. This nearly real-time ex vivo analysis may provide important feedback to the operator of the surgical instrument 1 during the surgical procedure and therefore assists in finding an accurate surgical resection plane.

Different techniques are available for nearly-real time ex-vivo tissue analysis of tissue passing the analysis sensor 11 in the discharge channel 7. Techniques that may be used to detect the presence of cancer cells in tissue passing the analysis sensor 11 for example include fiber optic spectroscopy, hyperspectral imaging, different techniques of Raman Spectroscopy and/or MicroCT imaging, or fluorescence spectroscopy or fluorescent imaging.

In particular Diffuse Reflectance Spectroscopy (DRS) may be applied, single fiber spectroscopy, multispectral imaging method, hyperspectral imaging method, fluorescence spectroscopy or imaging and different Raman spectroscopy techniques to analyse the presence of cancer cells in the pieces of tissue passing by. It is remarked that in fluorescence imaging chemical probes are introduced into the body of the patient that bind to the cells of the tissue to be removed, for example to the cancerous cells. This technology may facilitate to distinguish between healthy tissue and unhealthy tissue.

The sensor signal of the analysis sensor may be processed by the tissue analysis device 10, and fed after processing to the processing unit 6 of the surgical instrument 1 or may directly be fed to the processing unit 6. The processing unit 6 may function as a feedback device to provide a feedback signal, representative for the presence of cancer cells in the pieces of analysed tissue. The feedback signal may be used to signal a surgeon using the surgical instrument on the results of the analysis, for example by providing a visible or audible signal.

The sensor signal and/or feedback signal may also be fed to a central processing unit, in which the information can be further processed.

The tissue analysis device 10 provides analysis of tissue that already has been removed from the body of the patient. This offers the advantage that the analysed tissue is evidently also the tissue that is removed from the body of the patient. Furthermore, ex-vivo analysis may be more reliable in determining the presence of cancer cells in the tissue than in vivo techniques. However, the analysis can only be performed after the tissue has been removed from the body of the patient.

To allow analysis of the tissue to be removed before actual removal of the tissue, the surgical instrument 1 comprises a second tissue analysis device 12 comprising a second analysis sensor 13 in the form of an optical unit to optically analyse via an optical fiber or fibers 14 non-removed tissue a few millimetres in front of the tissue removal device 3.

The second analysis sensor is arranged in the part of the housing 2 having a larger cross section as this part provides proper space to arrange the optical unit 13. The optical fiber(s) 14 run(s) along the distal part of the surgical instrument 1 having a smaller cross-section to the distal end of the surgical instrument 1. The advantage of this arrangement is that the cross-section of the distal part only needs to comprise the optical fiber(s) 14 in order to analyse tissue in front of the tissue removal device 3, e.g. a few millimetres in distal direction of the tissue removal device 3.

In the shown embodiment, the second analysis sensor 13 is provided as a fiber optic spectroscopy device arranged for Diffuse Reflectance Spectroscopy in the visible and/or the NIR wavelength region. Diffuse Reflectance Spectroscopy has proved to be capable of distinguishing breast cancer from normal tissue based on differences in fat and water content with high accuracy. More details with respect to this technology may be found in US 2015/0005765, the contents of which are herein incorporated by reference, in its entirety.

Any other suitable technique to analyse tissue in front of the tissue removal device, such as for example hyperspectral imaging, multi spectral imaging or pH measurements or acoustic measurements, may also be applied.

The second tissue analysis device 12 allows the operator of the surgical instrument, e.g. a surgeon or surgical robot system, to verify whether the surgical instrument is correctly positioned in or in front of tissue containing cancer cells, before actual removal of the tissue is started.

Figure 2:
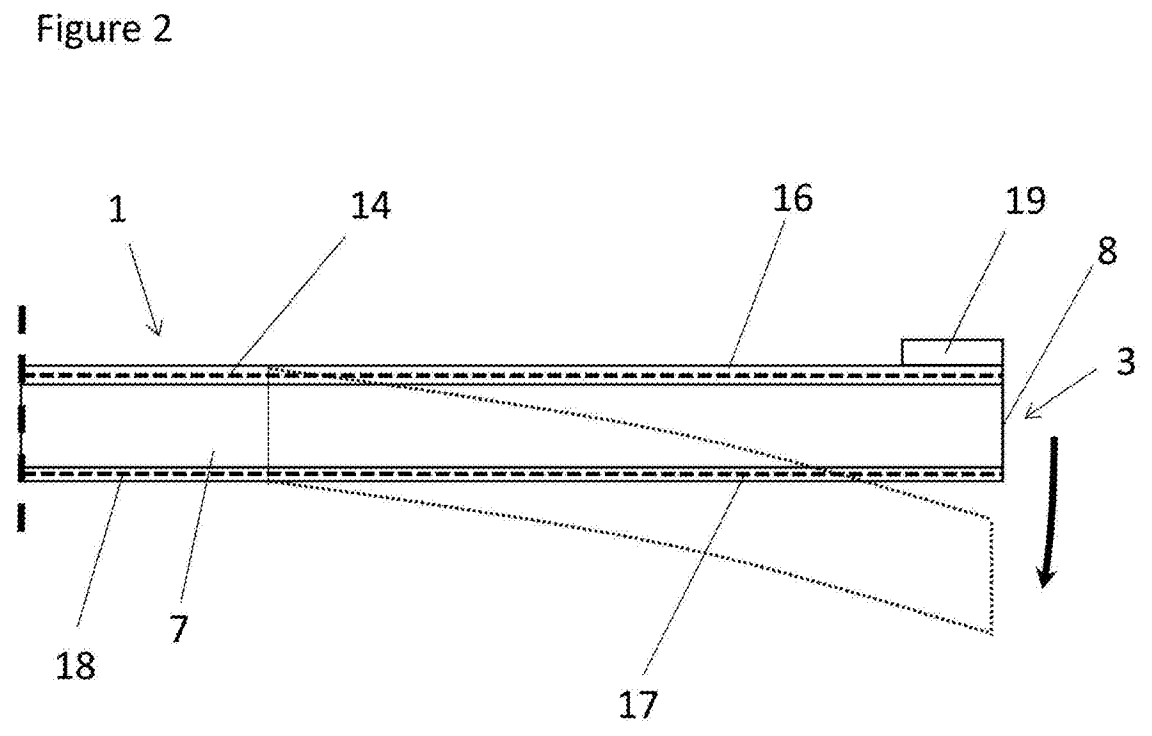

FIG. 2 shows the distal part of an alternative embodiment of the surgical instrument 1. The proximal part of the surgical instrument 1, not shown in FIG. 2, may be the same or substantially the same as the proximal part of the surgical instrument in FIG. 1.

The tissue removal device 3 of this embodiment is formed by a suction device formed by the inlet of the discharge channel 7. The underpressure used to transport removed tissue into and through the discharge channel 7 may also be used, in some types of tissue, to remove the tissue from the body of the patient without the need for other removal devices, such as the rotating cutting blade 4.

Further, the distal part of the surgical instrument 1 may comprise a bendable tip part 16 to adjust a position and/or orientation of the tissue removal device 3 with respect to a proximal part of the surgical instrument 1. The bendable tip part 16 is bendable in a single bending direction. In other embodiments, the tip part may be movable, in particular bendable in multiple directions. The bending direction of the bendable tip part 16 is indicated by an arrow, and a bended position of the bendable tip part 16 is shown in ghost lines.

The bending of the bendable tip part 16 may be controlled by an operator of the surgical instrument 1, for example by a pulling rod connected to the end of the distal tip part 16. The pulling of such pulling rod may be performed manually or by a linear actuator.

The bending of the bendable tip part 16 may facilitate manoeuvring of the surgical instrument 1, in particular the tissue removal device 3, in the body of the patient in order to properly align the tissue removal device 3 with tissue to be removed. For example, the location of the tissue removal device 3 may be changed by bending of the bendable tip part 16 without readjusting the position of the complete surgical instrument.

A position sensor in the form of a fiber Bragg grating 17 can be provided to enable the surgical instrument 1 to determine a position of the bendable tip part 16 with respect to the proximal part of the surgical instrument 1. It is advantageous for the operator to know the position of the bendable tip part 16. The fiber Bragg gratings is arranged in an optical fiber 18 that runs from the bendable tip part 16 to an interrogator device spaced from the fiber Bragg grating. The interrogator device may be used to determine the position of the bendable tip part 16 with respect to the proximal part of the surgical instrument may be determined.

The surgical instrument 1 further may comprise a tissue treatment device 19 for example a cryotreatment unit to freeze tissue before removal of the tissue, an electrocoagulation unit and/or an electromagnetic head for emitting radio waves. In some procedures it may be advantageous to treat the tissue before its actual removal, for example to prevent excessive bleeding during and after removal.

Figure 3:
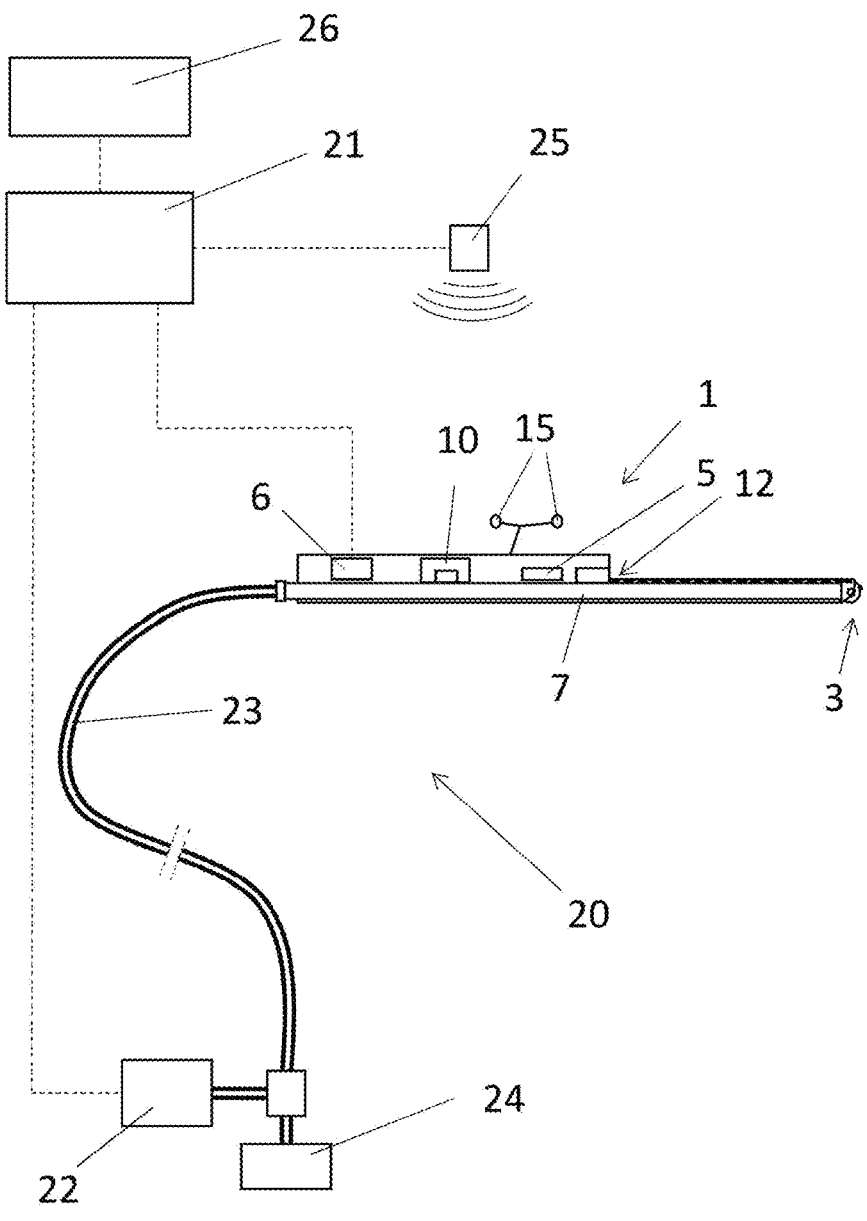
FIG. 3 shows schematically a first embodiment of a surgical system according to the invention comprising the surgical instrument of FIG. 1.

FIG. 3 shows a surgical system 20 comprising the surgical instrument 1 for use as a handheld instrument. The surgical system 20 comprises a central processing unit 21 connected to the processing unit 6 of the surgical instrument 1 to exchange relevant data and/or instructions.

The surgical system 20 may comprise an underpressure source 22 arranged to provide an underpressure to create a suction flow in the discharge channel 7 that continues through the conduit 23 to the underpressure source 22. Pieces of removed tissue that are drawn into the discharge channel 7 will travel through the conduit 23 of the discharge channel 7 towards the underpressure source 22. A receptacle 24 is connected to the conduit 23 to collect the removed tissue.

The surgical system 20 further comprises a position tracking system 25 arranged to track a 3D position of the surgical instrument 1 using one or more tracking markers 15 provided on the surgical instrument 1. It is remarked that the bendable tip part 16 of the surgical instrument shown in FIG. 2 may also comprise tracking markers to determine the position of the bendable tip part 16. The position tracking system (and position markers) may be an optical or an electromagnetic tracking system or other positioning system The underpressure source 22 and the position tracking system 25 are connected to the central processing unit 21.

Further, the surgical system 20 comprises a display device 26 to display relevant information with respect to the surgical procedure. This information may for example comprise results from the analysis performed by the ex vivo tissue analysis device 10 and/or the in vivo tissue analysis device 12. Also, the display device 26 may show an actual position of the surgical instrument 1 as determined by the position tracking system 25 in combination with pre-operative and/or intraoperative imaging data of the relevant part of the body of the patient to be treated.

Figure 4:
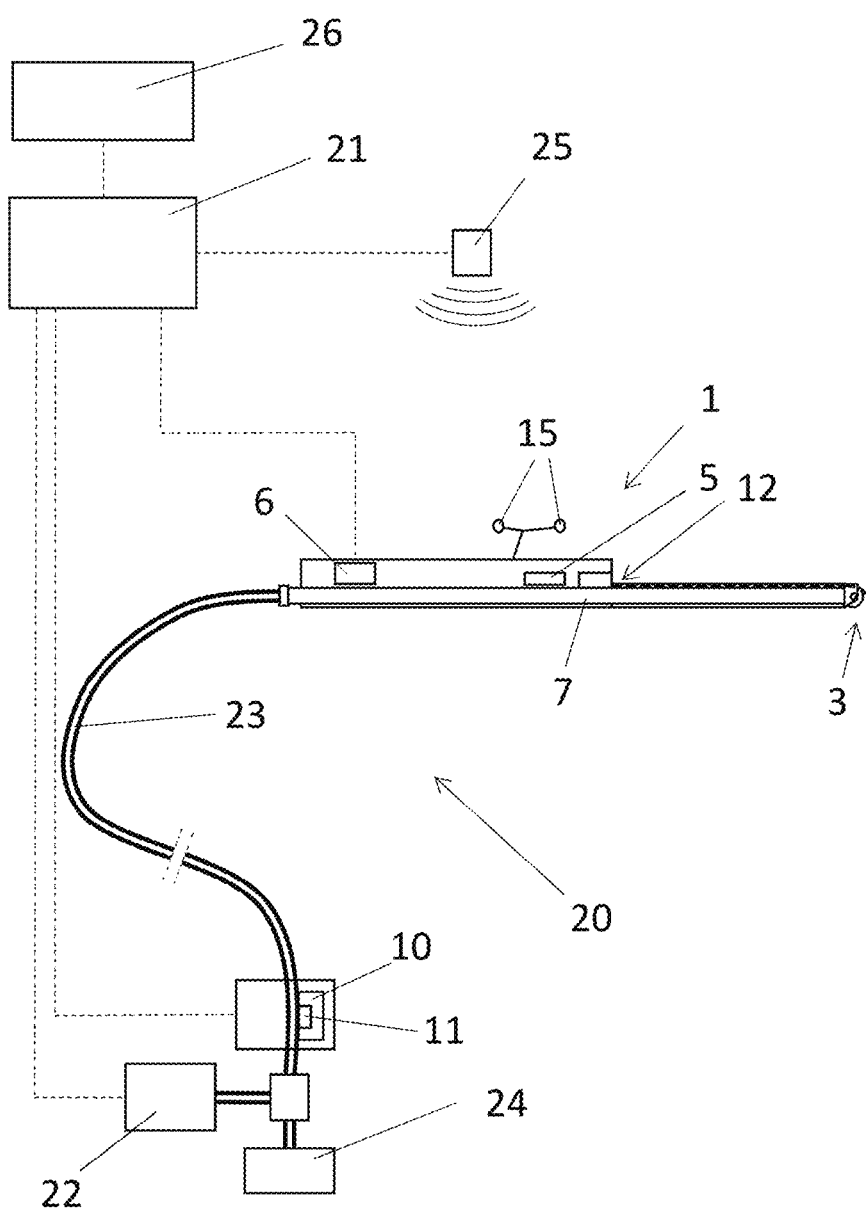
FIG. 4 shows schematically an alternative embodiment of a surgical system and a surgical system according to the invention.

FIG. 4 shows an alternative embodiment of the surgical instrument 1. In the surgical instrument 1 of FIG. 4, the tissue analysis device 10 is arranged outside the housing 2 of the part of the surgical instrument 1 that is held by an operator. The tissue analysis device 10 is arranged next to the conduit 23 of the discharge channel 7 so that the analysis sensor 11 may analyse removed tissue that passes through the conduit 23 of the discharge channel 7.

When the tissue analysis device 10 is relatively large or heavy it may be advantageous to place the tissue analysis device 10 outside the housing 2, for example at a stationary position as shown in FIG. 4. The time between removal of the tissue and the provision of the results of the tissue analysis may in such case be longer due to the time needed to transport the removed tissue to the tissue analysis device 10. However, this time may be sufficiently small to use the outcome of the tissue analysis device 10 as input for manoeuvring the surgical instrument 1 for the removal of tissue.

In yet another embodiment, a first ex vivo tissue analysis device may be arranged in the housing and a second ex vivo tissue analysis device may be arranged outside the housing.

Figure 5:
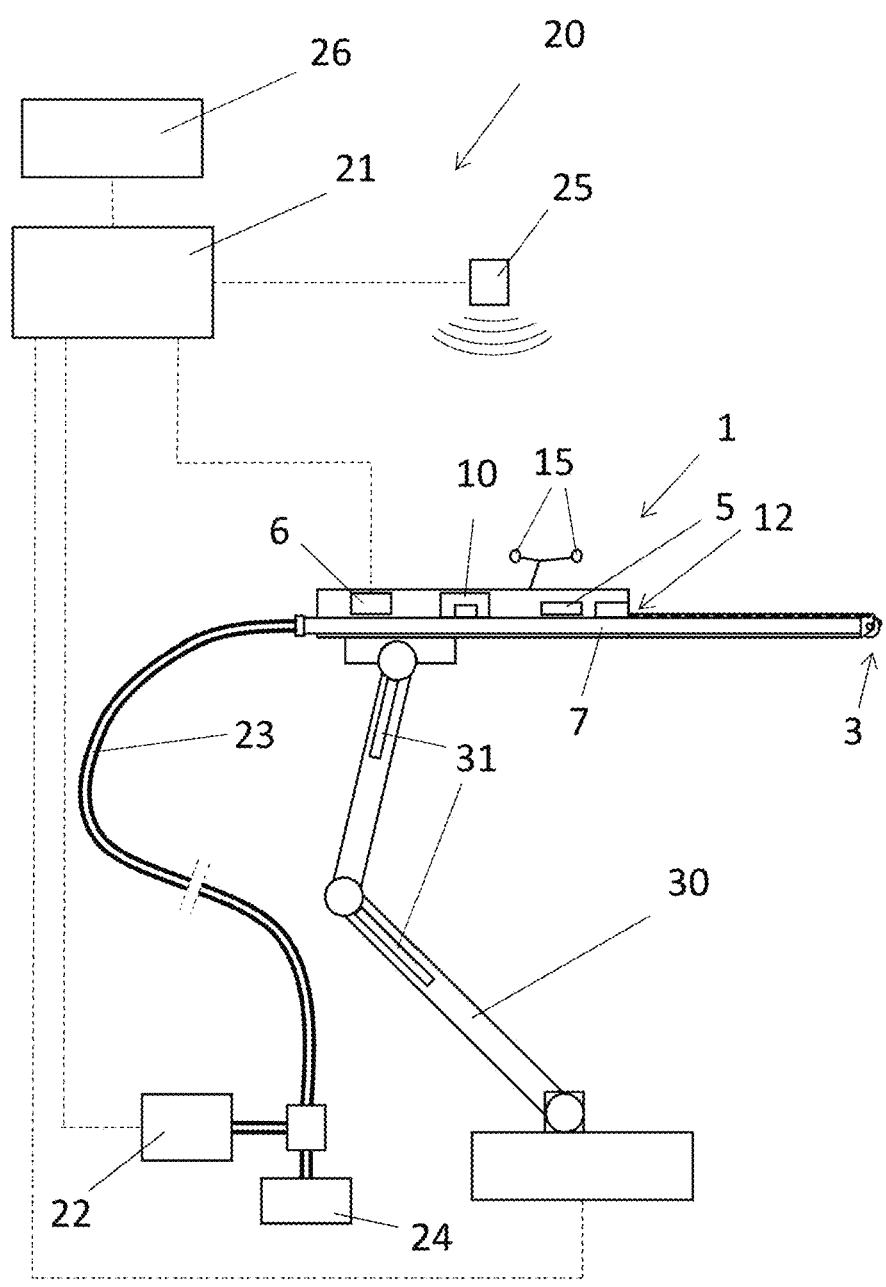
FIG. 5 shows schematically a second embodiment of a surgical system according to the invention comprising the surgical instrument of FIG. 1.

FIG. 5 shows another alternative embodiment of a surgical system 20 comprising the surgical instrument of FIG. 1.

The surgical system 20 also comprises, similar to the surgical system of FIG. 3, a central processing unit 21, an underpressure source 22 connected to the conduit 23 of the discharge channel 7, a receptacle 24, a position tracking system 25 and a display device 26.

In addition, the surgical system 20 may comprise a robotic arm 30 configured to hold and move the surgical instrument 1. On the basis of instructions provided by the central processing unit 21, the robotic arm 30 can be moved by actuators 31 to manipulate the position and orientation of the surgical instrument 1.

The robotic arm 30 in combination with pre-operative and/or intraoperative imaging data and 3D position tracking of the surgical instrument 1 enables the surgical system 20 to robotically navigate the surgical instrument to a desired location in front of or in center of a tumor to be removed.

When the surgical instrument 1 is arranged in the desired location, the second tissue analysis device 20 will be activated to analyse in vivo, using Diffuse Reflectance Spectroscopy or any other optical or non-optical technique as described earlier, whether the tissue directly in front of the tissue removal device 3 contains cancer cells.

When it is assured that the tissue in front of the tissue removal device 3 contains cancer cells, the central processing unit 21 may send a signal to the local processing unit 6 of the surgical instrument to activate the actuator 5 to rotate the cutting blade 4 to cut pieces of tissue from the tissue in front of the tissue removal device 3. The central processing unit 21 also activates the underpressure source 22 to create a suction flow in the discharge channel 7 to draw the cut pieces of tissue into the discharge channel 7 and move them towards the receptacle 24.

In the discharge channel 7, the removed pieces of tissue pass the tissue analysis device 10, where directly an analysis of the tissue takes place. As long as the analysed tissue contains cancer cells, the removal of pieces of tissue may continue. However, when it is detected that the removed pieces of tissue no longer contain cancer cells, the cutting of pieces of tissue is stopped, at least in the direction in which the surgical instrument 1 is moved. The tissue removal device 3 may, when needed be manoeuvred in another direction and/or position to continue the above procedure until all tissue containing cancer cells is removed from the body of the patient. The manoeuvring of the tissue removal device 3 may be carried out by controlling the robotic arm, but also by adjustment of the bending of the bendable part 16 of the distal part of the surgical instrument 1 as shown in FIG. 2.

The above procedure can be used to produce clean resection margins with a minimal removal of healthy tissue and hence optimal cosmetic result.

It is remarked that the pieces of removed tissue that are collected in the receptacle 22, are intact tissue part that can still be used for further analysis, for example post-surgery molecular analysis or standard histopathology analysis.

The procedure as described above, can also be used in the surgical system 20 shown in FIG. 3, whereby the manoeuvring of the surgical instrument to properly align the tissue removal device 3 with the tissue to be removed is performed by a surgeon holding the surgical instrument 1. The proper position and orientation of the surgical instrument may for example be obtained on the basis of images shown in the display device 26 that combine pre-operative and or intra-operative images with a real time 3D position of the surgical instrument 1.

Figure 6:
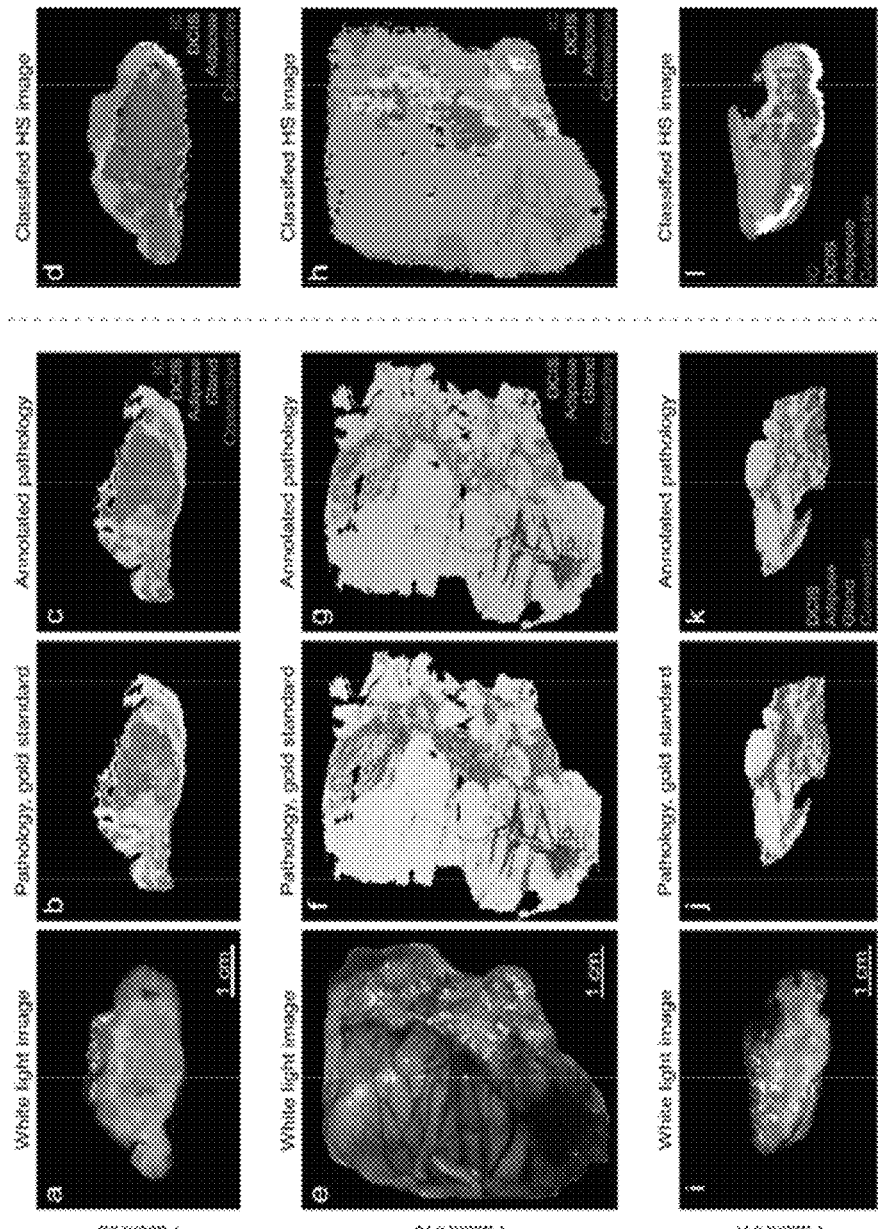
FIG. 6 shows a comparison between various classification methods, being performed on three specimen slices containing carcinoma pockets.

In FIG. 6, the results of the recent research into the hyperspectral imaging are displayed. In FIG. 6, three slices of tissue specimen are displayed in which carcinoma pockets are present. The left-most column, e.g. images a, e and i, show white light images of the slices. The second column, e.g. images b, f and j, displays the same slices with a histopathology classification being performed thereon and the third column, e.g. images c, g and k, displays an annotated view on the histopathological results. The right-most column, finally, e.g. images d, h and l, displays the specimen slices with the results of the hyperspectral imaging. In the hyperspectral images, similar as in the annotated pathology images, invasive carcinoma (IC) pockets are coloured red, ductal carcinoma in situ (DCIS) pockets are coloured pink, connective tissue is coloured green and fatty tissue is coloured blue.

Figure 7:
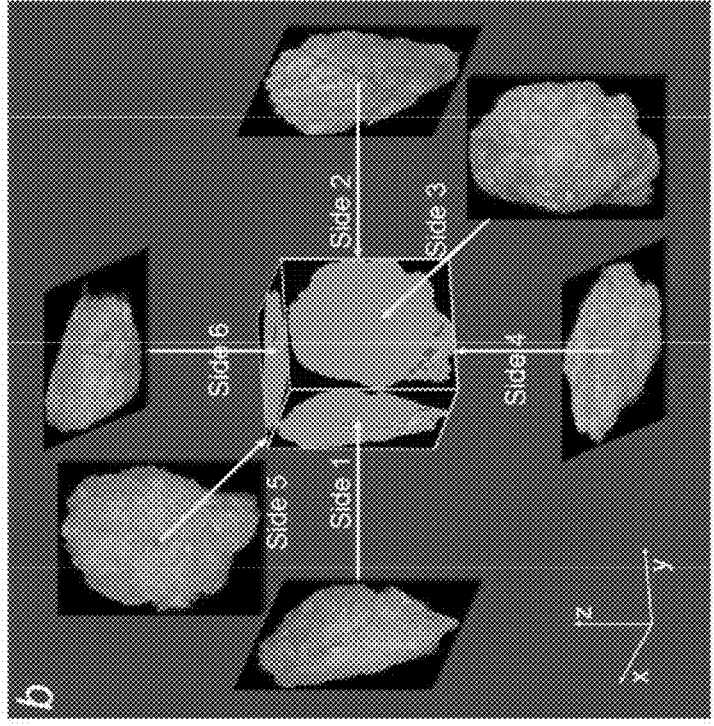
FIG. 7 shows a comparison between white light images and hyperspectral images of an unsliced specimen containing cancer.
Figure 7:
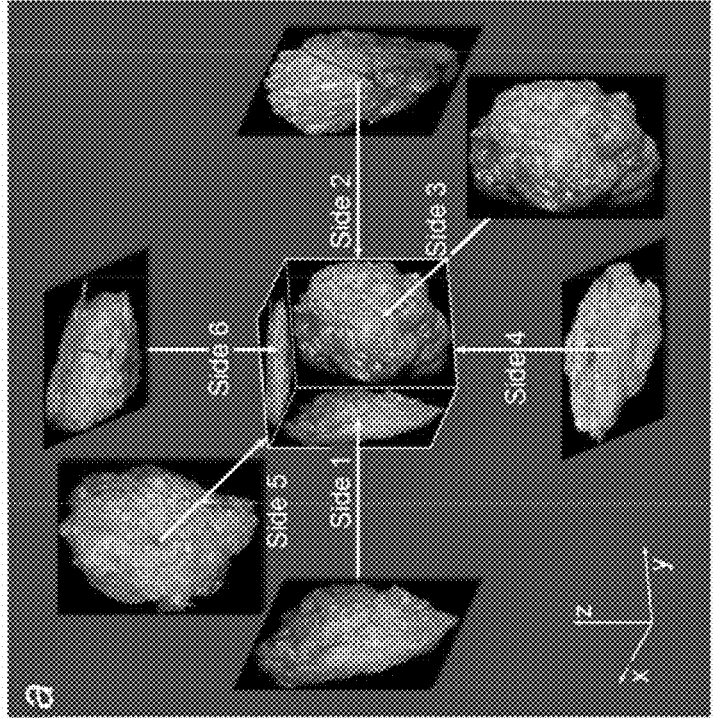

FIG. 7 displays a comparison between white light images (figure a) and hyperspectral images (figure b) of six faces of an unsliced specimen containing carcinoma. The hyperspectral images have been classified by means of the support vector machine (SVM) classification algorithm that has been developed by the applicant in his recent research. In figure b, the red and pink areas indicate areas in the tissue of which the classification algorithm suspects the presence of cancer.

It will be understood that in alternative implementations of the above-described detailed embodiments, the ex-vivo tissue analysis device 10 may be omitted.

FIG. 8 illustrates a surgical instrument with a needle 801 in form of a trocar forming a hollow shaft. FIG. 8A shows a perspective view of a part of the needle. FIG. 8B shows a side view of the surgical instrument with the needle. FIG. 8C shows a top view of the surgical instrument with the needle.

The needle 801 has a form of a hollow shaft comprising an outer wall 814 around an inner cavity 815, an interior of the needle providing a space for positioning the second surgical instrument coaxially to the needle 801 at least partly inside the needle 801 and movable with respect to the needle in an axial direction of the needle 801.

The needle 801 has at least one optic fiber 802 that extends from a proximal sensing device (not shown), up to a distal tip 807 of the needle. The sensing device may be similar to the second analysis sensor 13 of FIG. 1, and may be in the form of an optical unit to optically analyse via the optical fiber 802 or fibers 802, 805 non-removed tissue a few millimetres in front of the needle. It is noted that when an instrument with a tissue removal device is inserted through the needle, the front of the needle may coincide with the front of the tissue removal device, as will be described below.

The distal end 803 of the optic fiber 802 is located at the distal tip 807 of the needle 801. The needle 801 may have a second optic fiber 805 that extends from the proximal sensing device, to the distal tip 807 of the needle. The distal end 806 of the second optic fiber 805 is located at the distal tip 807 of the needle 801. More optic fibers may be provided to add more measurement points. The ends of those additional optic fibers may be at the distal tip 807, a bit proximal of the distal tip 807, or even a bit distal of the distal tip 807. At any given time, one of the optic fibers may be used as light emitter while the other optic fibers may be used as light receivers. The role of light emitter may be performed by different ones of the optic fibers in succession. The distal end 803 of the first optic fiber 802 and the distal end 806 of the second optic fiber 805 may be disposed on opposite sides of the needle tip 807, as illustrated. This allows an optic measurement to be performed of the tissue just distal of the needle tip 807, in between the two ends 803 and 806. However, the exact location of the distal ends 803, 805 of the optic fibers 802, 805 is not limited to opposite sides of the distal tip 807 of the needle. These distal ends 803, 805 may be anywhere at (or near) the needle tip 807. The needle may have an opening 804 that may coincide with a replaceable tissue removal device.

Figure 8A:
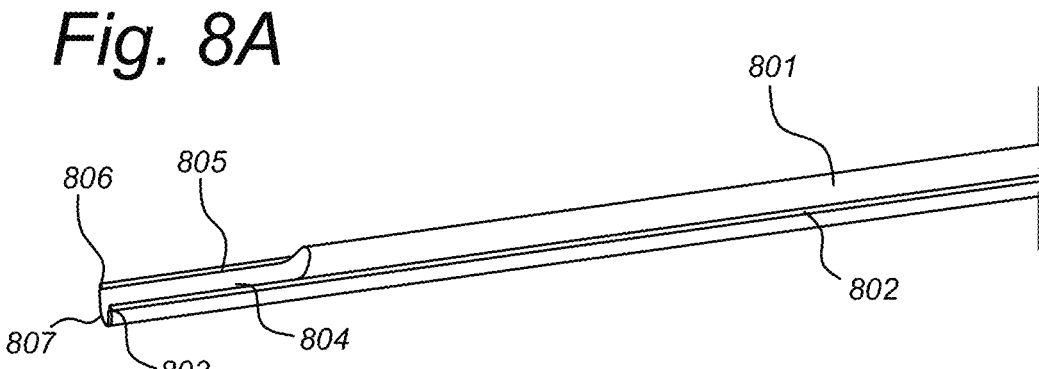
FIG. 8A shows a perspective view of a needle in form of a trocar forming a hollow shaft.
Figure 8B:
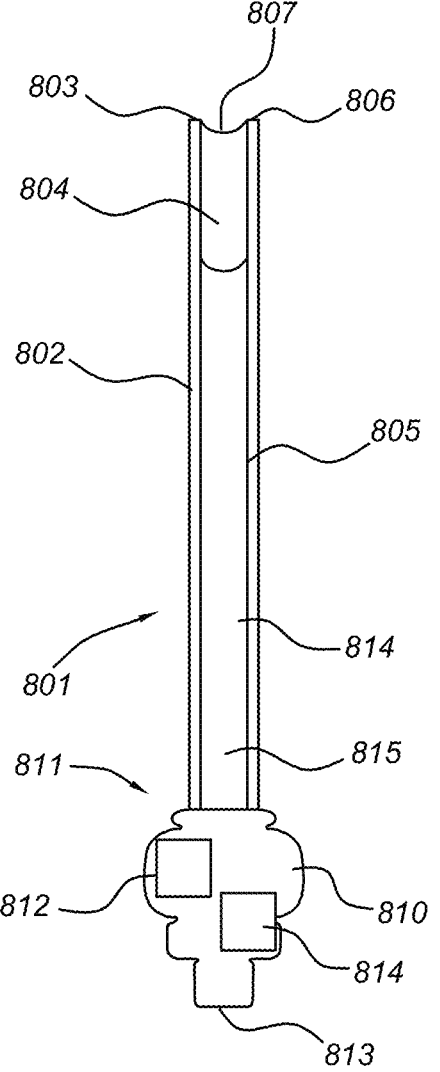
FIG. 8B shows a top view of the needle.
Figure 8C:
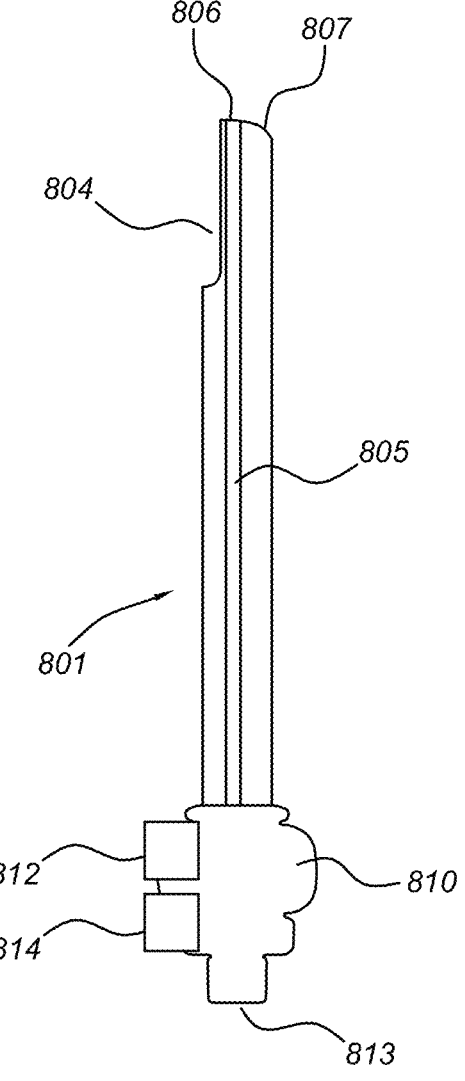
FIG. 8C shows a side view of the needle.

As shown in FIG. 8B and FIG. 8C, the surgical instrument may comprise the needle 801 and a housing 810. The surgical instrument may comprise a tissue analysis device 811 comprising an analysis sensor 812 in the form of an optical unit to optically analyse via the optical fiber or fibers 802, 805 non-removed tissue a few millimetres in front of the tip 807 of the needle 801. The tissue analysis device 811 is configured to provide a sensor signal representative of an analysed characteristic of the tissue, in particular for the presence of unhealthy tissue or cancer cells within the tissue.

The analysis sensor 812 is arranged in the part of the housing 810 having a larger cross section as this part provides proper space to arrange the optical unit 812. The optical fiber(s) 802, 805 run(s) along the distal part of the surgical instrument having a smaller cross-section to the distal end 807 of the surgical instrument. The advantage of this arrangement is that the cross-section of the distal part only needs to comprise the optical fiber(s) 802, 805 in order to analyse tissue in front of the tip 807 of the needle 801, e.g. a few millimetres in distal direction of the tip 807 of the needle 801. This is only an example implementation. The analysis sensor 812 may also be implemented separate of the housing 810, wherein the optic fiber(s) 802, 805 are connected to the analysis sensor 812.

The at least one optic fiber 802, 805 may extend from the tissue analysis sensor 812 to the distal tip 807 of the needle 801. The optic fiber(s) 802, 805 may be integrated in the outer wall 814 of the needle 801.

In the shown embodiment, the analysis sensor 812 is provided as a fiber optic spectroscopy device arranged for Diffuse Reflectance Spectroscopy in the visible and/or the NIR wavelength region. Diffuse Reflectance Spectroscopy has proved to be capable of distinguishing breast cancer from normal tissue based on differences in fat and water content with high accuracy. The technique may also be used for distinguishing otherwise unhealthy tissue from normal tissue. More details with respect to this technology may be found in US 2015/000576, the contents of which are herein incorporated by reference, in its entirety.

Any other suitable technique to analyse tissue in front of the tissue removal device, such as for example hyperspectral imaging, multi spectral imaging or pH measurements or acoustic measurements, may also be applied.

The tissue analysis device 811 allows the operator of the surgical instrument, e.g. a surgeon or surgical robot system, to verify whether the surgical instrument is correctly positioned in or in front of tissue containing cancer cells (or otherwise unhealthy tissue), before actual removal or treatment of the tissue is started using a device for tissue removal or tissue treatment, inserted through the needle from the proximal end 813 up to the distal tip 807 of the needle 801.

The surgical instrument with the needle, being referred to hereinafter as first surgical instrument, may cooperate with a second surgical instrument. The second surgical instrument fits inside the inner space 815 of the hollow shaft 814 of the needle 801 and may comprise a tissue removal device arranged at a distal end of the second surgical instrument. Moreover, the second surgical instrument may comprise a discharge channel connected to the tissue removal device for discharge of removed tissue. The first surgical instrument may comprise an actuator 814 to retract the needle while the tissue removal device is kept in place. This actuator may comprise a step motor, for example. However, this is only an example implementation of the actuator 814. The analysis device 811 may be configured to scan the tissue at a plurality of positions along the tissue removal device as the needle is retracted.

Figure 8D:
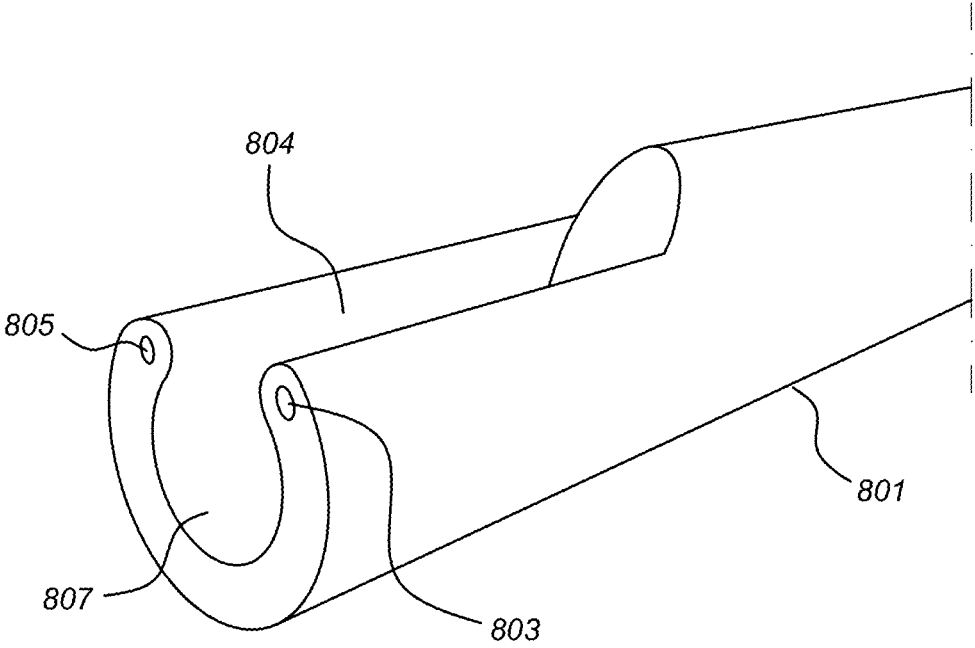
FIG. 8D shows a tip 807 of a needle in detail.

FIG. 8D shows a close-up of the tip 807 of an implementation of the needle 801, in which the optic fibers are integrated in the material of the needle, so that only the tips 803 and 805 of the optic fibers are visible and exposed.

Figure 9:
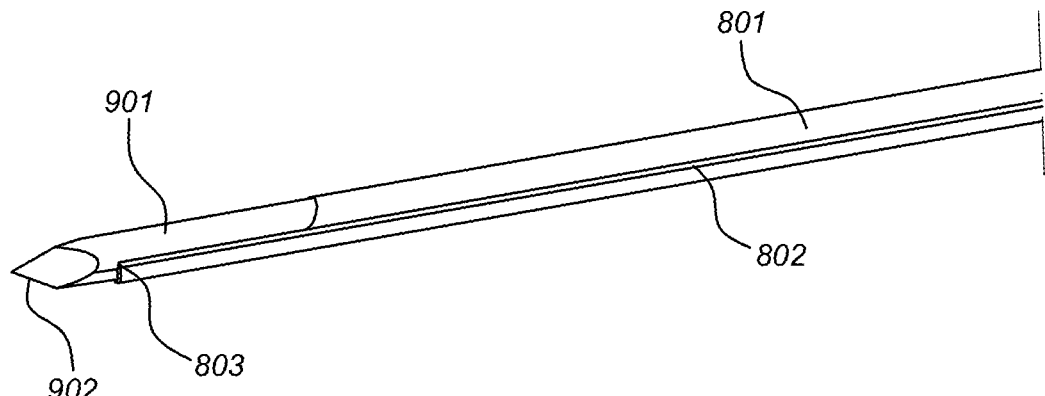
FIG. 9 illustrates a needle with a stylet disposed therein.

FIG. 9 illustrates the needle 801 having a stylet 901 disposed therein. The stylet may have a sharp distal end 902. This configuration is suitable for inserting the needle in the tissue and finding a spot with certain tissue characteristics (e.g. tumor cells) measured by the optic fiber ends 803, 806. The suspect regions can be identified with the use of spectroscopy at the needle tip. Once the needle 801 is in the correct place, the stylet 901 is replaced with an instrument for tissue removal. It is observed that the use of a stylet is not a limitation of the present disclosure. For example, the needle 801 may be suitable to be inserted into the tissue by itself, without stylet, or with another suitable surgical instrument, such as a surgical instrument for tissue removal shown in FIG. 10 or 12, being placed in the needle.

It is noted that tissue measurements with the stylet in place, in some implementations and depending for example on the measurement principle used and the relative position of the optic fiber tips 803, 806, may only work when the stylet is not obstructing the optic path between the two optic fibers. In such a case, the stylet may be retracted a little bit after puncturing and before performing the tissue measurement, so that the stylet is not in between the distal tips 803 and 806 of the optic fibers 802 and 805 during the measurement.

Figure 10:
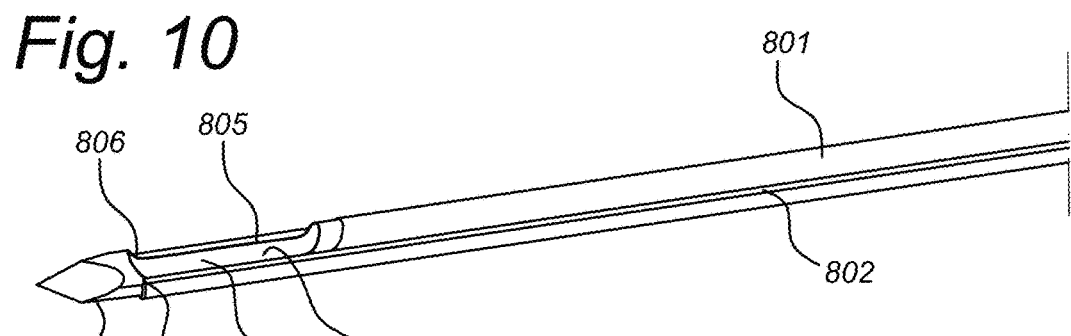
FIG. 10 illustrates a needle with an instrument for tissue removal disposed therein.

FIG. 10 illustrates the needle 801 having the instrument 1001 for tissue removal disposed therein. The needle 801 has an opening 804 that coincides with the opening 1002 of the instrument 1001 for tissue removal. In use, the specimen can be sucked into the opening using vacuum applied from a proximal side of the instrument 1001. Since the ends 803 and 806 of the optic fibers 802 and 805 are at the edge of the opening 804, the tissue of the specimen in the opening 804, 1002 can be analysed. In this way, the entire biopsy specimen can be analysed in multiple increments.

Figure 11A:
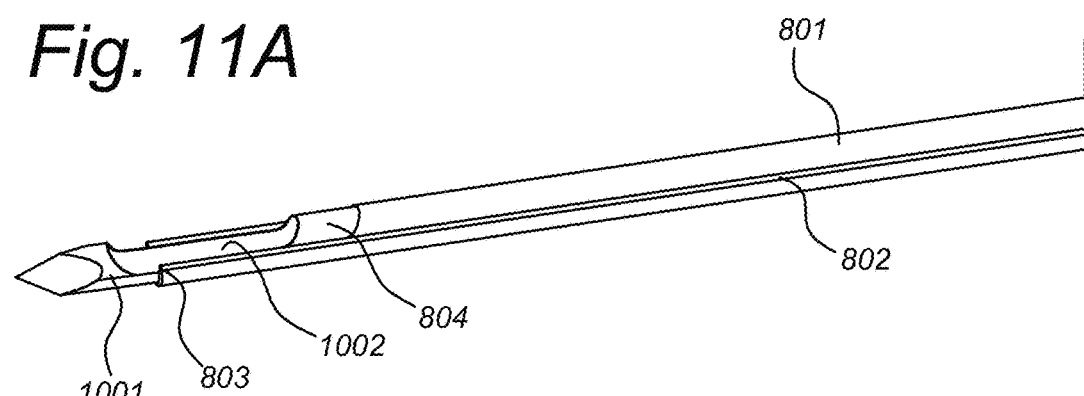
FIG. 11A and FIG. 11B show a needle that is retracted.
Figure 11B:
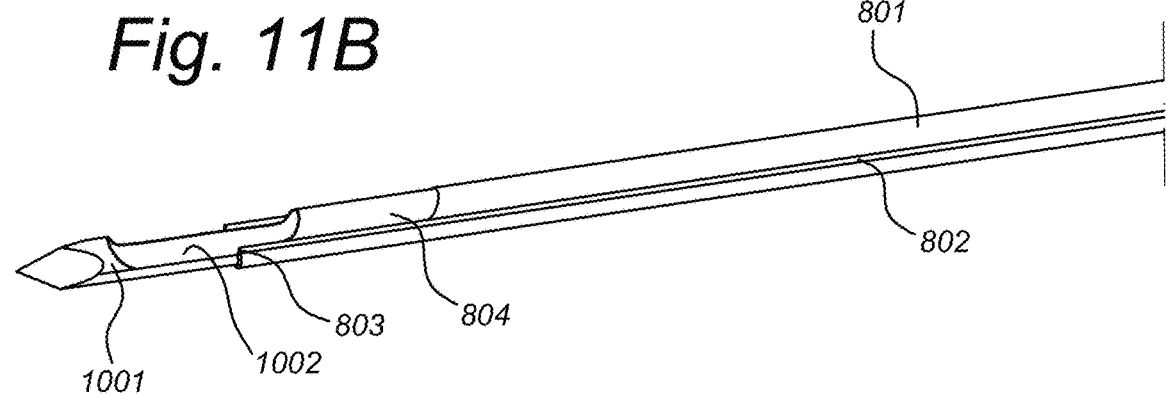

FIG. 11A and FIG. 11B show that the needle 801 may be retracted in steps (or in a continuous movement), while keeping the instrument 1001 in place. Along the way, the tissue in the opening 1002 may be measured at several places since the ends 803, 806 move along the opening 1002.

Figure 12:
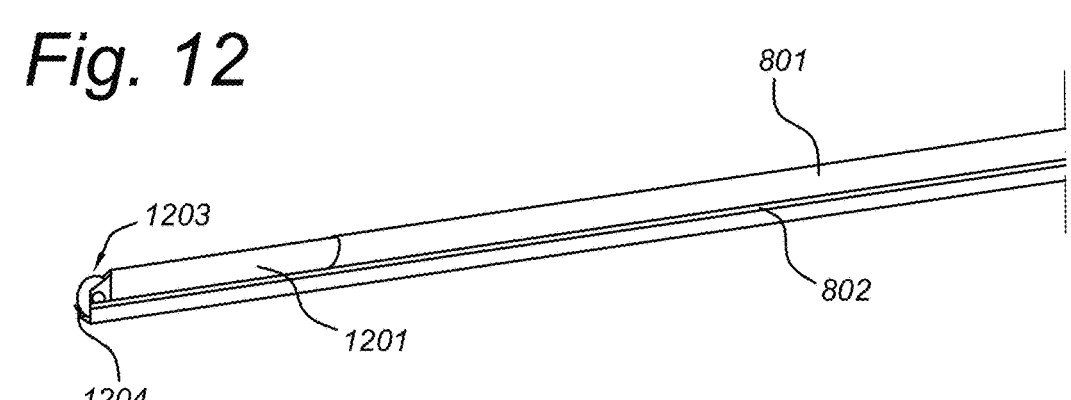
FIG. 12 shows a needle with another example of an instrument for tissue removal disposed therein.

FIG. 12 shows the needle 801 together with a surgical instrument 1201 for tissue removal disposed in the needle 801. The instrument 1201 for tissue removal comprises a tissue removal device 1203 that is similar to the tissue removal device 3 of FIG. 1. The tissue removal device 1203 is arranged at the distal end of the surgical instrument 1201. The tissue removal device 1203 comprises a cutting blade 1204 that is mounted on a rotatable element that can be driven in a rotating movement by an actuator (not illustrated), similar to the cutting blade 4 of FIG. 1. The actuator may, for example, be activated by a user of the surgical instrument, for instance by pressing a button, and/or by a processing unit of the surgical instrument 1201. The configuration and operation of the tissue removal device 1203 has been described in detail hereinabove. When the surgical instrument 1201 is disposed in the needle 801 as shown in FIG. 12, the distal end 803 of optic fiber 802, and optionally the distal end 806 of optic fiber 805 of the needle 801 is close to the tissue removal device 1203, so that the tissue can be examined by means of the optic fiber of the needle 801 before being cut by the surgical instrument 1201.

In certain embodiments disclosed herein, the surgical instrument comprises a cutting device to facilitate removal of tissue from the body of the patient. The tissue removal device may be provided with a cutting device configured to cut pieces of tissue distal to the distal tip of the surgical instrument. The cutting device may be any device, for example a cutting blade, that is capable of cutting pieces of tissue from the body of the patient, at a location where the cut pieces of tissue can easily and reliably move into the distal end of the discharge channel to discharge the pieces of tissue through the discharge channel. This cutting blade may be a rotatable cutting blade. However, this is not a limitation. For example, the cutting blade may be configured to perform another type of movement, such as a linear movement.

Instead of, or in addition to, suction, active transport may be employed to transport the removed tissue through the surgical instrument. Another optical measurement method that may be used with the first or second tissue analysis device (for ex-vivo or in-vivo tissue analysis) is fluorescence lifetime imaging. Another tissue treatment device that may be employed may include a microwave unit, a radiofrequency unit, or an electroporation unit.

It has been found that hyperspectral imaging, in a wavelength range between 940 nm and 1650 nm, preferably between 600 nm and 1650 nm, more preferably between 400 nm and 1650 nm, is suitable for use in optical measurements to detect carcinoma, e.g. cancer cells, in tissue specimen.

In an embodiment, the second analysis sensor is a tissue analysis device based on for instance optical techniques, using Diffuse or subdiffuse Reflection, second or third Harmonic generation, Fluorescence, either from native chromophores in the tissue, fluorescing metabolites, or from exogenously administered molecules, either using single- or multi-photon excitation or using Raman scattering, executed either in a hyperspectral or multispectral imaging geometry, or as a point measurement technique, or a low coherence imaging system. Additionally the tissue analysis device could comprise an ultrasound sensor, a photoacoustic sensor, an electronic impedance sensor or pH sensitive detector may also be applied. such as a fiber optic spectroscopy device, or a hyperspectral imaging or fluorescent imaging device or multifibre optical devices at the tip of the surgical instrument. Fiber optic spectroscopy, fluorescent imaging, fluorescent life time imaging, second harmonic hyperspectral, multispectral or multifibre spectroscopy may be used for Diffuse Reflectance Spectroscopy (DRS) or fluorescence imaging or hyperspectral or multispectral imaging in the visible and/or near infrared (NIR) wavelength region. Single- or multiphoton fluorescence measurements or imaging can be based on the native fluorescence of the tissue or may use exogenously administered florescent molecules These analyses may be used to differentiate normal healthy breast tissue form cancerous breast tissue. These analyses may also be used to differentiate normal healthy tissue of any other organ form cancerous tissue of that organ, or otherwise unhealthy tissue of that organ. For example, the needle 801 may be used to analyse any desired kind of tissue or organ. DRS has proved to be capable of distinguishing in vivo invasive carcinoma from normal tissue based on differences in fat and water content with high accuracy.

Any other suitable technique to analyse tissue in front of the tissue removal device, such as for example optical techniques, using Diffuse or subdiffuse Reflection, second or third Harmonic generation, Fluorescence, either from native chromophores in the tissue, fluorescing metabolites, or from exogenously administered molecules, either using single- or multi-photon excitation or using Raman scattering, executed either in a hyperspectral or multispectral imaging geometry, or as a point measurement technique, or a low coherence imaging system. Additionally the tissue analysis device could comprise an ultrasound sensor, a photoacoustic sensor, an electronic impedance sensor or pH sensitive detector may also be applied.

The following subject-matter is disclosed herein in form of clauses.

1. Surgical instrument to remove tissue, in particular tissue containing cancer cells, from a body and to analyse the removed tissue, comprising:
    a tissue removal device arranged at a distal end of the surgical instrument;
    a discharge channel connected to the tissue removal device for discharge of removed tissue; and
    a tissue analysis device, comprising an analysis sensor arranged to analyse removed tissue passing through the discharge channel, wherein the tissue analysis device is configured to provide a sensor signal representative for an analysed characteristic of the removed tissue, in particular for the presence of cancer cells within the removed tissue.

2. The surgical instrument of clause 1, wherein the analysis sensor is a fiber optic spectroscopy device, multispectral imaging device, hyperspectral imaging device, Raman Spectroscopy or other Raman based technology, a fluorescence spectroscopy device, a fluorescence imaging device, a Low Coherence Tomographic system, a MicroCT imaging device or an acoustic sensor.

3. The surgical instrument of clause 1 or 2, wherein the surgical instrument comprises an elongated housing, wherein the discharge channel at least partially runs through the housing, and wherein the tissue analysis device is arranged in the housing.

4. The surgical instrument of any of the clauses 1-3, wherein the tissue removal device comprises a suction device.

5. The surgical instrument of any of the clauses 1-4, wherein the surgical instrument comprises a cutting device.

6. The surgical instrument of clause 5, wherein the cutting device comprises a rotatable cutting blade configured to cut slices of tissue.

7. The surgical instrument of clause 1, wherein a proximal end of the discharge channel is connectable to an underpressure source to create a suction flow in the discharge channel.

8. The surgical instrument of any of the clauses 1-8, wherein the surgical instrument comprises a second tissue analysis device comprising a second analysis sensor to analyse non-removed tissue in front of the tissue removal device.

9. The surgical instrument of clause 8, wherein the second analysis sensor is a single fiber spectroscopy, a multi-fiber spectoscopy device, multispectral imaging device, hyperspectral imaging device, fluorescence spectroscopy or imaging device, a Raman device or pH sensor.

10. The surgical instrument of any of the clauses 1-9, wherein the surgical instrument comprises one or more tracking markers arranged to enable a position tracking system to track a position of the surgical instrument.

11. The surgical instrument of any of the clauses 1-10, wherein the surgical instrument comprises a feedback device to provide a feedback signal on the basis of the sensor signal representative for the analysed characteristic of the removed tissue or the in vivo measurements on the tissue that is intended to be removed, in particular the presence of cancer cells within the removed tissue or the intended tissue to be removed.

12. The surgical instrument of any of the clauses 1-11, wherein the distal part of the surgical instrument comprises a movable part, for example a bendable part, to adjust a position and/or orientation of the tissue removal device with respect to a proximal end of the surgical instrument, wherein movement of the movable part can be controlled by an operator.

13. The surgical instrument of clause 12, wherein the surgical instrument comprises a position sensor system to determine a position of the movable part.

14. The surgical instrument of any of the clauses 1-13, wherein the surgical instrument comprises at or near its distal end a tissue treatment device for treatment of the tissue before removal of the tissue.

15. A surgical system to remove tissue, in particular tissue containing cancer cells, from a body and to analyse the removed tissue, comprising:

the surgical instrument of any of the preceding clauses, and an underpressure source connected to a proximal end of the discharge channel to create a suction flow in the discharge channel.

16. The surgical system of clause 15, wherein the surgical instrument comprises one or more tracking markers, and wherein the surgical system comprises a position tracking system to track a position of the surgical instrument using the one or more tracking markers.

17. The surgical system of clause 15 or 16, wherein the surgical system comprises a central processing unit configured to monitor the removal of tissue by the surgical instrument.

18. The surgical system of any of the clauses 13-17, wherein the surgical system is a surgical robot system, wherein the surgical system comprises one or more actuators to control a position of the surgical instrument.

19. The surgical system of any of the clauses 13-18, wherein the surgical system comprises a receptacle directly or indirectly connected to the discharge channel to collect removed tissue.

The invention claimed is:

1. A surgical instrument to remove tissue, in particular unhealthy tissue or tissue containing cancer cells, from a body and to analyse the removed tissue, comprising:

an elongate housing;

a tissue removal device arranged at a distal end of the surgical instrument, wherein the tissue removal device is configured to remove tissue directly distally from the tissue removal device;

wherein the tissue removal device comprises a cutting device, wherein the cutting device comprises a rotatable cutting blade configured to cut slices of tissue, wherein the rotatable cutting blade is mounted on a rotatable element adapted to be driven in a rotating movement by an actuator to rotate around an axis that is perpendicular to a longitudinal axis of a discharge channel;

the discharge channel formed by a tube connected to the tissue removal device for discharge of removed tissue, wherein the discharge channel at least partially runs through the elongate housing from the distal end of the surgical instrument connected to the tissue removal device; and a tissue analysis device comprising an analysis sensor to analyse non-removed tissue in front of the tissue removal device, wherein the tissue analysis device is configured to analyse the non-removed tissue in front of the tissue removal device based on diffuse reflectance spectroscopy in a visible wavelength region or a near infrared wavelength region, wherein the tissue analysis device is configured to provide a sensor signal representative for an analysed characteristic of the non-removed tissue, in particular for the presence of the unhealthy tissue or the cancer cells within the tissue, wherein the tissue analysis device further comprises at least two optic fibers along a distal part of the surgical instrument to the distal end of the surgical instrument, wherein the tissue analysis device is configured to emit light through a first optic fiber of the at least two optic fibers while receiving light through another optic fiber of the at least two optic fibers, and wherein the distal ends of the at least two optic fibers are at opposite sides of the distal end of the surgical instrument, and wherein the analysis sensor is arranged in a part of the elongate housing that has a larger cross section than the distal part of the surgical instrument.

2. The surgical instrument of claim 1, comprising a further tissue analysis device, comprising a further analysis sensor arranged to analyse the removed tissue passing through the discharge channel, wherein the further tissue analysis device is configured to provide a further sensor signal representative for a further analysed characteristic of the removed tissue, in particular for the presence of the unhealthy tissue or the cancer cells within the removed tissue, wherein the further analysis sensor is a fiber optic spectroscopy device, multispectral imaging device, hyperspectral imaging device, Raman Spectroscopy or other Raman based technology, a fluorescence spectroscopy device, a fluorescence imaging device, a fluorescence life time imaging device, a Low Coherence Tomographic system, a MicroCT imaging device or an acoustic sensor.

3. The surgical instrument of claim 2, wherein the further tissue analysis device is arranged in the elongate housing.

4. The surgical instrument of claim 1, wherein the tissue removal device comprises a suction device.

5. The surgical instrument of claim 1, wherein a proximal end of the discharge channel is connectable to an underpressure source to create a suction flow in the discharge channel.

6. The surgical instrument of claim 1, wherein the analysis sensor is a multifiber spectroscopy device.

7. The surgical instrument of claim 1, wherein the surgical instrument comprises one or more tracking markers arranged to enable a position tracking system to track a position of the surgical instrument.

8. The surgical instrument of claim 1, wherein the surgical instrument comprises a feedback device to provide a feedback signal on the basis of the sensor signal representative for the analysed characteristic of the non-removed tissue, in particular the presence of the unhealthy tissue or cancer cells within the removed tissue or the non-removed tissue.

9. The surgical instrument of claim 1, wherein the distal part of the surgical instrument comprises a bendable part, to adjust a position or orientation of the tissue removal device with respect to a proximal end of the surgical instrument, wherein movement of the bendable part can be controlled by an operator, wherein the surgical instrument comprises a position sensor system to determine a position of the bendable part, wherein the position sensor system comprises a relative position sensor configured to determine a position of the bendable part with respect to the proximal end of the surgical instrument.

10. The surgical instrument of claim 1, wherein the surgical instrument comprises at or near its distal end a tissue treatment device for treatment of the tissue before removal of the tissue, wherein the tissue treatment device comprises a cryotreatment unit, an electrocoagulation unit, an electromagnetic head for emitting radio waves, a microwave unit, a radiofrequency unit, or an electroporation unit.

11. The surgical instrument of claim 2, wherein the surgical instrument comprises a feedback device to provide a feedback signal on the basis of the further sensor signal representative for the analysed characteristic of the removed tissue and the sensor signal representative for the analysed characteristic of the non-removed tissue, in particular the presence of unhealthy tissue or cancer cells within the removed tissue or the non-removed tissue.

12. The surgical instrument of claim 1, wherein the distal part of the surgical instrument comprises a bendable part to adjust a position or orientation of the tissue removal device with respect to a proximal end of the surgical instrument, wherein movement of the bendable part can be controlled by an operator.

13. A surgical system to remove tissue, in particular tissue containing unhealthy tissue or cancer cells, from a body and to analyse the removed tissue, comprising:

the surgical instrument of claim 1, and an underpressure source connected to a proximal end of the discharge channel to create a suction flow in the discharge channel.

14. The surgical system of claim 13, wherein the surgical instrument comprises one or more tracking markers, and wherein the surgical system comprises a position tracking system to track a position of the surgical instrument using the one or more tracking markers.

15. The surgical system of claim 13, wherein the surgical system comprises a central processing unit configured to monitor the removal of tissue by the surgical instrument.

16. The surgical system of claim 13, wherein the surgical system is a surgical robot system, wherein the surgical system comprises one or more actuators to control a position of the surgical instrument.

17. The surgical system of claim 13, wherein the surgical system comprises a receptacle directly or indirectly connected to the discharge channel to collect removed tissue.

* * * * *